United States Patent
Appel et al.

(10) Patent No.: US 10,481,291 B2
(45) Date of Patent: Nov. 19, 2019

(54) CHEMICALLY-SELECTIVE IMAGER FOR IMAGING FLUID OF A SUBSURFACE FORMATION AND METHOD OF USING SAME

(71) Applicant: SHELL OIL COMPANY, Houston, TX (US)

(72) Inventors: Matthias Appel, Houston, TX (US); Benjamin Charles Anger, Houston, TX (US); Hilko de Jong, Houston, TX (US); Lynn Faith Gladden, Cambridge (GB); Michael David Mantle, Cambridge (GB); Andrew John Sederman, Cambridge (GB); Nicholas Philip Ramskill, Cambridge (GB)

(73) Assignee: SHELL OIL COMPANY, Houston, TX (US)

( * ) Notice: Subject to any disclaimer, the term of this patent is extended or adjusted under 35 U.S.C. 154(b) by 166 days.

(21) Appl. No.: 15/448,183

(22) Filed: Mar. 2, 2017

(65) Prior Publication Data
US 2017/0254920 A1 Sep. 7, 2017

Related U.S. Application Data

(60) Provisional application No. 62/303,238, filed on Mar. 3, 2016.

(51) Int. Cl.
*G01V 3/00* (2006.01)
*G01V 3/32* (2006.01)
(Continued)

(52) U.S. Cl.
CPC ............ *G01V 3/32* (2013.01); *E21B 47/0002* (2013.01); *E21B 49/06* (2013.01); *E21B 49/10* (2013.01);
(Continued)

(58) Field of Classification Search
CPC ...... E21B 47/0002; E21B 49/06; E21B 49/10; E21B 47/06; E21B 47/065; G01R 33/5617; G01R 33/4828; G01V 3/32; G01N 24/081
(Continued)

(56) References Cited

U.S. PATENT DOCUMENTS

| 4,769,602 A | 9/1988 | Vinegar et al. |
| 6,047,239 A | 4/2000 | Berger et al. |

(Continued)

OTHER PUBLICATIONS

Mitchell, Magnetic Resonance Core Analysis At 0.3T, International Symposium of the Society of Core Analysts held in Avignon, France, Sep. 8-11, 2014. (Year: 2014).*

(Continued)

*Primary Examiner* — Rodney E Fuller

(57) ABSTRACT

An imager and method for imaging fluid of a subsurface formation is disclosed. The imager includes a housing having a sidewall defining a passage to receive a core sample of the subsurface formation therethrough. The housing is positioned in a downhole tool and has a fluid inlet to receive fluid from the subsurface formation into the passage. The imager also includes a permanent magnet positioned in the sidewall of the housing, a radio frequency coil positioned in the sidewall of the housing between the permanent magnet and the passage, a gradient field in the sidewall of the housing between the permanent magnet and the radio frequency coil, and a chemically-selective imager. The chemically-selective imager is operatively connected to the radio frequency coil to selectively pulse frequencies according to a pulse sequence whereby individual fluid measurements of the sample are generated.

12 Claims, 7 Drawing Sheets

(51) Int. Cl.
| | |
|---|---|
| *E21B 47/00* | (2012.01) |
| *E21B 49/06* | (2006.01) |
| *E21B 49/10* | (2006.01) |
| *G01N 24/08* | (2006.01) |
| *G01R 33/48* | (2006.01) |
| *G01R 33/561* | (2006.01) |
| *E21B 47/06* | (2012.01) |

(52) U.S. Cl.
CPC ........ *G01N 24/081* (2013.01); *G01R 33/4828* (2013.01); *G01R 33/5611* (2013.01); *G01R 33/5617* (2013.01); *E21B 47/06* (2013.01); *E21B 47/065* (2013.01)

(58) Field of Classification Search
USPC .......................................................... 324/303
See application file for complete search history.

(56) References Cited

U.S. PATENT DOCUMENTS

| | | | |
|---|---|---|---|
| 6,220,371 | B1 | 4/2001 | Sharma et al. |
| 6,897,652 | B2 | 5/2005 | Appel et al. |
| 8,499,856 | B2 | 8/2013 | Kumar |
| 9,133,709 | B2 | 9/2015 | Huh et al. |
| 2009/0219019 | A1* | 9/2009 | Taherian .............. G01N 24/081 324/303 |
| 2011/0234220 | A1* | 9/2011 | Mitchell .............. G01N 24/081 324/303 |
| 2012/0209541 | A1* | 8/2012 | Ong .......................... G01F 1/74 702/45 |
| 2014/0253116 | A1* | 9/2014 | Freedman .............. G01R 33/30 324/303 |

OTHER PUBLICATIONS

Edelstein, W. A., Hutchison, J. M. S., Johnson, G. & Redpath, T., Spin warp NMR imaging and applications to human whole-body imaging, Physics in Medicine and Biology 25, 751 (1980).
Mitchell, J., Chandrasekera, T.C., Holland, D.J., Gladden, L.F. and Fordham, E.J., Magnetic resonance imaging in petrophysical core analysis, Physics Reports, 526, pp. 165-225 (2013).
Hennig, J., Nauerth, A. & Friedburg, H, RARE imaging: a fast imaging method for clinical MR. Magnetic resonance in medicine: official journal of the Society of Magnetic Resonance in Medicine / Society of Magnetic Resonance in Medicine 3, 823-833 (1986).
Mansfield, P. Multi-planar image formation using NMR spin echoes, Journal of Physics C: Solid State Physics 10, L55-L58 (1977).
M. Benning, L.F. Gladden, D.J. Holland, C.-B. Schonlieb, T. Valkonen, Phase reconstruction from velocity-encoded MRI measurements—a survey of sparsity-promoting variational approaches, Journal of Magnetic Resonance. 238 (2014) 26-43.
Lustig, M., Donoho, D. L., Santos, J. M. & Pauly, J. M, Compressed Sensing MRI. IEEE Signal Processing Magazine 25, 72-82 (2008).
Lustig, M., Donoho, D. & Pauly, J. M., Sparse MRI: The application of compressed sensing for rapid MR imaging. Magnetic resonance in medicine☐: official journal of the Society of Magnetic Resonance in Medicine / Society of Magnetic Resonance in Medicine 58, 1182-95 (2007).
Chang, C.T., Edwards, C.M., 1993, Proton MR Two-Component Chemical Shift Imaging of Fluids in Porous Media, The Log Analyst, 34, pp. 20-28.
Dereppe, J.M., Moreaux, C., Chemical Shift Imaging of Fluid Filled Porous Rocks, Magnetic Resonance Imaging, 9, pp. 809-813 (1991).
Dereppe, J.M., Moreaux, C., 2D Spin-Echo and 3D Chemical-Shift-Imaging Techniques for Analysis of Oil-Water Replacement in Limestone. Journal of Magnetic Resonance, 91, pp. 596-603 (1991).
Maudsley, A.A., Hila,I, S.K., Perman, W.H., Simon, H.E, Spatially Resolved High Resolution Spectroscopy by "Four-Dimensional" NMR. Journal of Magnetic Resonance, 51, pp. 147-152 (1983).
Dechter, James J., Komoroski, Richard A., Ramaprasad, S., Use of Presaturation for Chemical-Shift Selective Imaging of Individual Fluids in Sandstone and Carbonate Cores, Journal of Magnetic Resonance, 93, pp. 142-150 (1991).

* cited by examiner

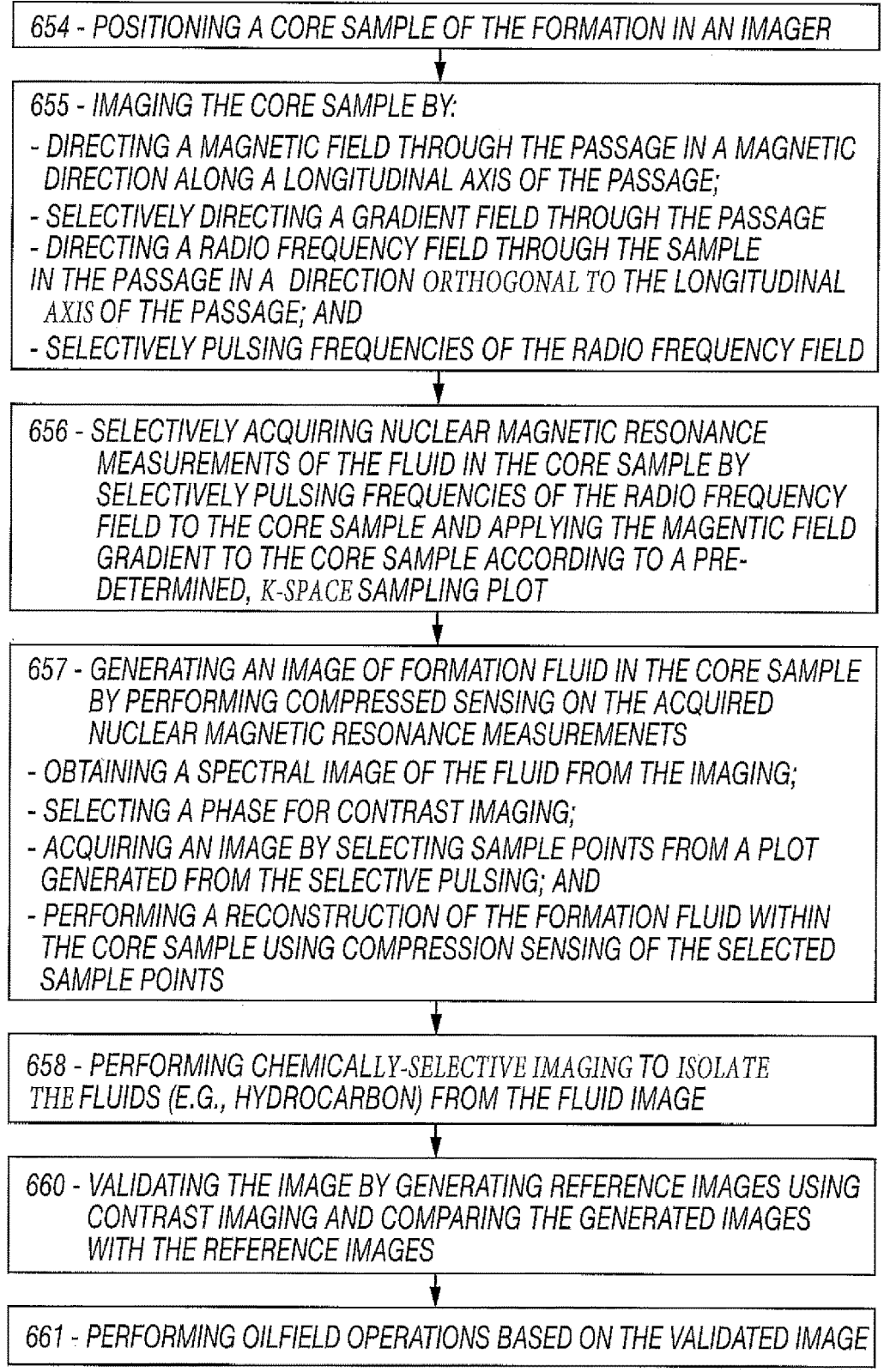

CHEMICALLY-SELECTIVE IMAGER FOR IMAGING FLUID OF A SUBSURFACE FORMATION AND METHOD OF USING SAME

The present application claims the benefit of pending U.S. Provisional Application Ser. No. 62/303,238, filed Mar. 3, 2016, the entire disclosure of which is hereby incorporated by reference.

BACKGROUND OF THE INVENTION

The present disclosure relates generally to formation evaluation. More specifically, the present disclosure relates to formation evaluation techniques, such as imaging of subsurface formations and fluids therein.

Exploration may be used to locate valuable hydrocarbons, such as oil and gas. Rigs are located at wellsites to drill wellbores and deploy tools downhole to locate subsurface reservoirs. Downhole tools, such as drilling tools, are advanced into the wellbore. Downhole tools, such as wireline tools, are deployed by a cable into the wellbore to collect subsurface samples for evaluation.

Downhole tools are often provided with logging devices, such as a nuclear magnetic resonance device to image subsurface formations. Downhole tools are also provided with sampling tools, such as probes, to draw samples of subsurface fluid into the downhole tool, and coring tools, such as axial and sidewall coring devices, to cut samples of subsurface formations. Examples of downhole tools are provided in U.S. Pat. Nos. 6,047,239 and 6,897,652.

Collected samples are captured in the downhole tool and retrieved to the surface. Samples are taken to labs for testing. Tests are performed on the samples to determine the presence of hydrocarbons. In some cases, core samples may be tested using nuclear magnetic resonance. Examples of testing are provided in U.S. Pat. Nos. 9,133,709, 8,499,856, 6,220,371 and 4,769,602.

Despite advancement in formation testing and sampling, there remains a need for techniques and tools capable of accurately evaluating subsurface formations.

SUMMARY OF THE INVENTION

In at least one aspect, the present invention is directed to an imager for imaging fluid of a subsurface formation. The imager includes a housing having a sidewall defining a passage to receive a core sample of the subsurface formation therethrough. The housing is positioned in a downhole tool and has a fluid inlet to receive fluid from the subsurface formation and into the passage. The imager also includes a permanent magnet positioned in the sidewall of the housing oriented to direct a magnetic field through the passage, a radio frequency coil positioned in the sidewall of the housing between the permanent magnet and the passage oriented to direct a radio frequency field through the passage, a magnetic field gradient positioned in the sidewall of the housing between the permanent magnet and the radio frequency coil to selectively direct a gradient field through the passage, and a chemically-selective imager operatively connected to the radio frequency coil to selectively pulse frequencies according to a pulse sequence whereby individual fluid measurements of the core sample are generated.

In another aspect, the present invention is directed to a method of imaging fluid positioned in a subsurface formation. The method involves positioning a core sample of the subsurface formation in a passage of an imager in a downhole tool, flooding the core sample by passing fluid from the formation into the passage, and imaging the flooded core sample. The imaging involves directing a magnetic field through the passage in a direction along a longitudinal axis of the passage, selectively directing a gradient field through the passage, selectively pulsing by directing a radio frequency field through the passage in a direction orthogonal to the direction of the magnetic field and the longitudinal axis of the passage, and generating images of the fluid in the core sample during the pulsing.

Finally, in another aspect, the present invention is directed to a method of imaging fluid located in a subsurface formation. The method involves positioning a core sample of the subsurface formation in a fluid filled passage of an imager, directing a magnetic field through the passage in a direction along a longitudinal axis of the passage, selectively directing a gradient field through the passage, directing a radio frequency field through the passage in the direction along the longitudinal axis of the passage, selectively acquiring nuclear magnetic resonance measurements of the fluid in the core sample by selectively pulsing frequencies of the radio frequency field to the core sample and applying the magnetic field gradient to the core sample according to a pre-determined, k-space sampling plot, and generating images of the fluid in the core sample by performing compressed sensing on the on the acquired nuclear magnetic resonance measurements.

BRIEF DESCRIPTION OF THE DRAWINGS

A more particular description of the disclosure, briefly summarized above, may be had by reference to embodiments thereof that are illustrated in the appended drawings. It is to be noted, however, that the appended drawings illustrate example embodiments of this disclosure and are, therefore, not to be considered limiting of its scope. The figures are not necessarily to scale, and certain features and certain views of the figures may be shown exaggerated in scale or in schematic in the interest of clarity and conciseness.

FIG. 6 is a flow chart depicting a method of imaging fluid in a subsurface formation.

DETAILED DESCRIPTION OF THE INVENTION

In the following description, numerous details are set forth to provide an understanding of the present disclosure. However, it will be understood by those skilled in the art that the present disclosure may be practiced without these details and that numerous variations or modifications from the described embodiments are possible.

Techniques for chemically-selective imaging of a subsurface formation are disclosed. These techniques involve performing magnetic resonance imaging (MRI) (or nuclear magnetic resonance (NMR) imaging) of core samples of the subsurface formation. The imaging may be performed in situ and/or at the surface using a device capable of selectively applying magnetic field pulses oscillating at radio frequency at the core samples. The chemically-selective imaging may image any NMR-active species (e.g. $^1$H or $^{23}$Na) using single or multi-tuned probes. Contrast imaging (e.g., relaxation and/or diffusion) may also be performed for comparison.

The imaging may be performed to selectively measure various fluids, such as hydrocarbons (e.g. crude oil or dodecane) and aqueous fluids (e.g., water, brine, etc.), in the core sample. Such techniques may be used to image the various fluids in the formation separately or in combination. In particular, the imaging may be used to differentiate between aqueous fluids and hydrocarbons in the core samples. These images may be used, for example, to characterize fluid parameters, such as rate of flow and type of hydrocarbons produced. Information gathered from such imaging may be used, for example, to identify specific fluids, individually image fluids, evaluate the formation containing the fluid, determine downhole parameters, detect valuable hydrocarbons, provide information for planning oilfield operations, among others.

The imaged fluids may be selectively imaged using, for example, 1D, 2D or 3D pulse sequences. To facilitate the imaging (e.g., to reduce acquisition time), various imaging sequences, such as fast imaging (rapid acquisition with relaxation enhancement (RARE) pulse sequencing) for collecting reduced sample sizes of the data and compressed sensing (CS) for reconstructing images from the reduced sample sizes, may be used. Fast imaging techniques may be used in combination with compressed sensing to reduce the image acquisition time which may be used, for example, to minimize the time that a tool is spent downhole performing the imaging.

Figure 1B:
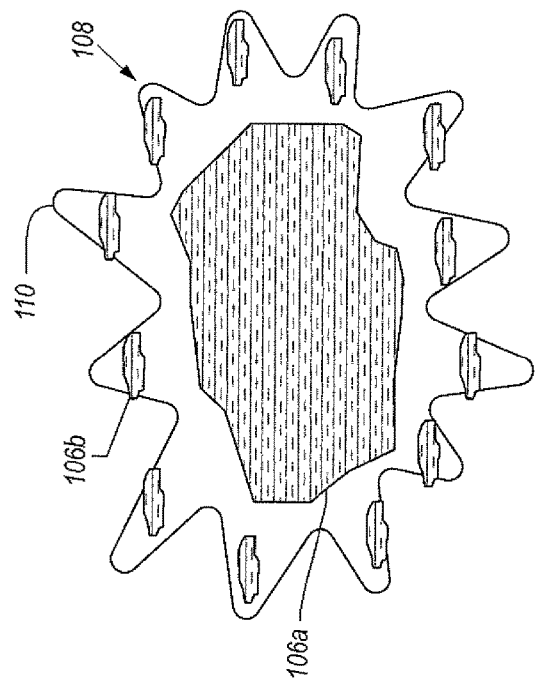
FIG. 1B is an expanded view of a pore in subterranean formation.
Figure 1A:
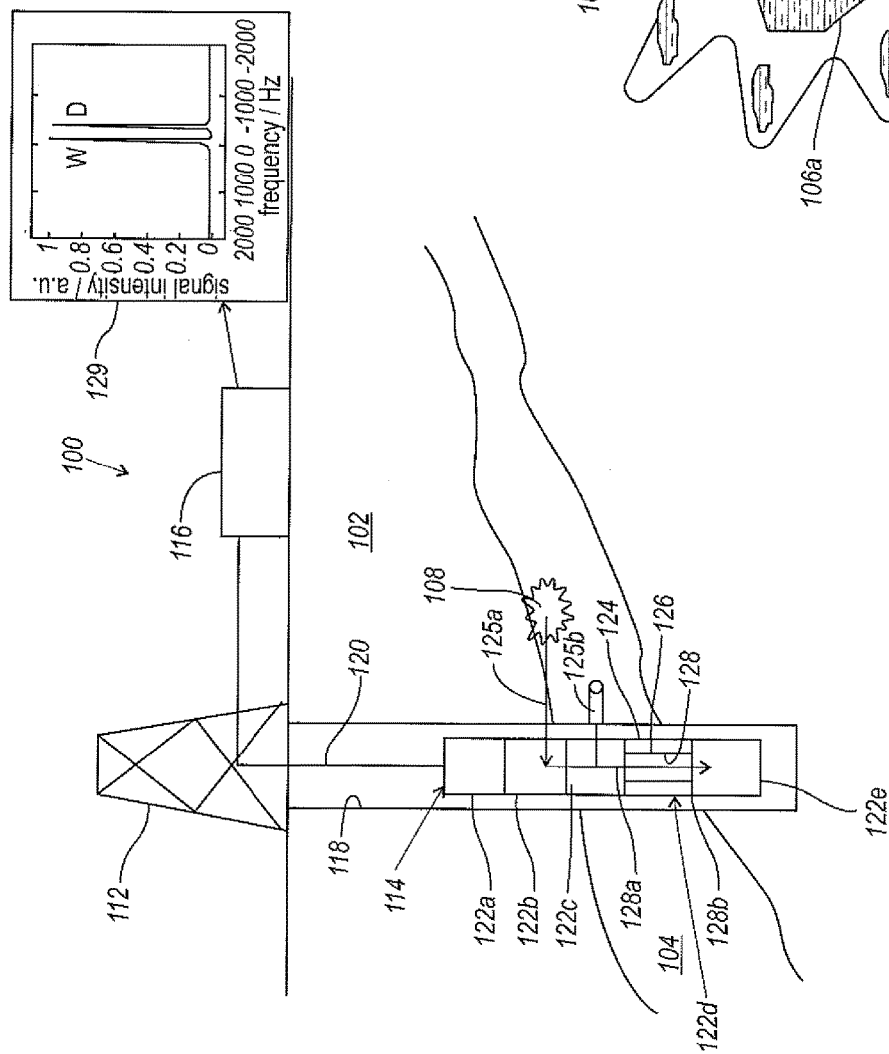
FIG. 1A is a schematic diagram depicting a wellsite with a downhole tool deployed into a wellbore penetrating a subsurface formation having fluid therein, the downhole tool having an imager therein.

FIG. 1A is a schematic diagram depicting a wellsite 100 for performing subsurface operations. The wellsite 100 is positioned about a subterranean formation 102 having a reservoir 104 with fluid therein. The formation 102 has one or more pores 108 with fluid therein. As shown in FIG. 1B, an expanded view of pore 108, a portion 106a of the fluid may be positioned centrally within the pore 108 and a portion 106b may be positioned in recesses 110 of the pore 108. The central portion 106a may represent retrievable fluids and the portion 106b may represent trapped fluids within the pore 108.

As shown, the wellsite 100 includes a rig 112, a downhole tool 114, and a surface unit 116. The downhole tool 114 is deployed into a wellbore 118 to measure subsurface parameters. The downhole tool 114 as shown is a wireline tool deployed into the wellbore 118 via a wireline cable 120, but any downhole tool (e.g., drilling, coiled tubing, production, and/or other tool) may be used. The wireline cable 120 is in communication with the surface unit 116 for passing signals therebetween. The surface unit 116 may be used to collect data from the downhole tool 114 and/or to send signals (e.g., power, command, etc.) to the downhole tool 114.

The downhole tool 114 of FIG. 1A may include a variety of components for performing various operations. As shown, the downhole tool 114 includes electronics 122a, a fluid sampler 122b, a core sampler 122c, an imager 122d, and a collector 122e. The electronics may include various devices, such as power, control, processing, communication (e.g., telemetry), and/or other devices used in downhole operations.

The fluid sampler 122b may be a conventional sampling tool capable of drawing fluid samples from the subsurface formation into the downhole tool 114. The core sampler 122c may be a conventional sidewall coring tool capable of cutting core samples 125b from a wall of the wellbore surrounding the formation. While FIG. 1A shows a sidewall coring example, an axial coring tool may be provided in the downhole tool 114. The collector 122e may be a receptacle for storing the collected samples. An example of a wireline tool with sampling capabilities is provided in U.S. Pat. No. 6,047,239.

The imager 122d as shown includes a housing 124 with a sidewall 126 defining a passage 128 therethrough. The fluid sampler 122b and the core sampler 122c may be positioned about (e.g., uphole from) the imager 122d to pass fluid samples 125a and core samples 125b, respectively, through an inlet 128a and into the passage 128 for measurement as schematically indicated by the arrows. The imager 122d may include, for example, a magnetic resonance imager (MRI) configured to receive the fluid and core samples 125a,b as is described further herein.

The core sample 125b may be imaged using the imager 122d. The core sample 125b may be passed through a passage inlet 128a (e.g., a door) located in the housing disposed to receive the core sample into the passage whereupon the core sample may be positioned in the passage 128 of the imager 122d. The core sample 125b may be saturated with the fluid sample (or other fluid) 125a using core flooding as indicated by the arrows. The fluid and core samples 125a,b may be released (e.g., dropped) from the passage 128 through an outlet 128b (e.g., a door) and into the collector 122e for storage and/or retrieval. The downhole tool 114 may be provided with various devices to facilitate and/or control sampling and/or imaging. For example, the fluid sample 125a may be free to pass through the imager 122d, or controlled using fluid control devices, such as flowlines, valves, etc.

The imager 122d may be capable of performing an MRI on the core sample within the downhole tool 114. The core sample 125b may be saturated with the sampled fluid during imaging. The measurements taken by the imager 122d may be collected by the surface unit 116 and outputs 129, such as a plot, may be generated therefrom as is described further herein.

Additional measurements may be taken using sensor(s) and/or other devices to determine various subsurface parameters, such as downhole conditions, formation parameters, fluid parameters, etc. For example, the downhole tool 114 may be provided with optical fluid analyzers, gauges, spectrometers, transducers, etc. that may collect additional measurements, such as composition, temperature, pressure, etc. The collected images and/or measurements may be evaluated to determine various subsurface parameters.

Figure 2:
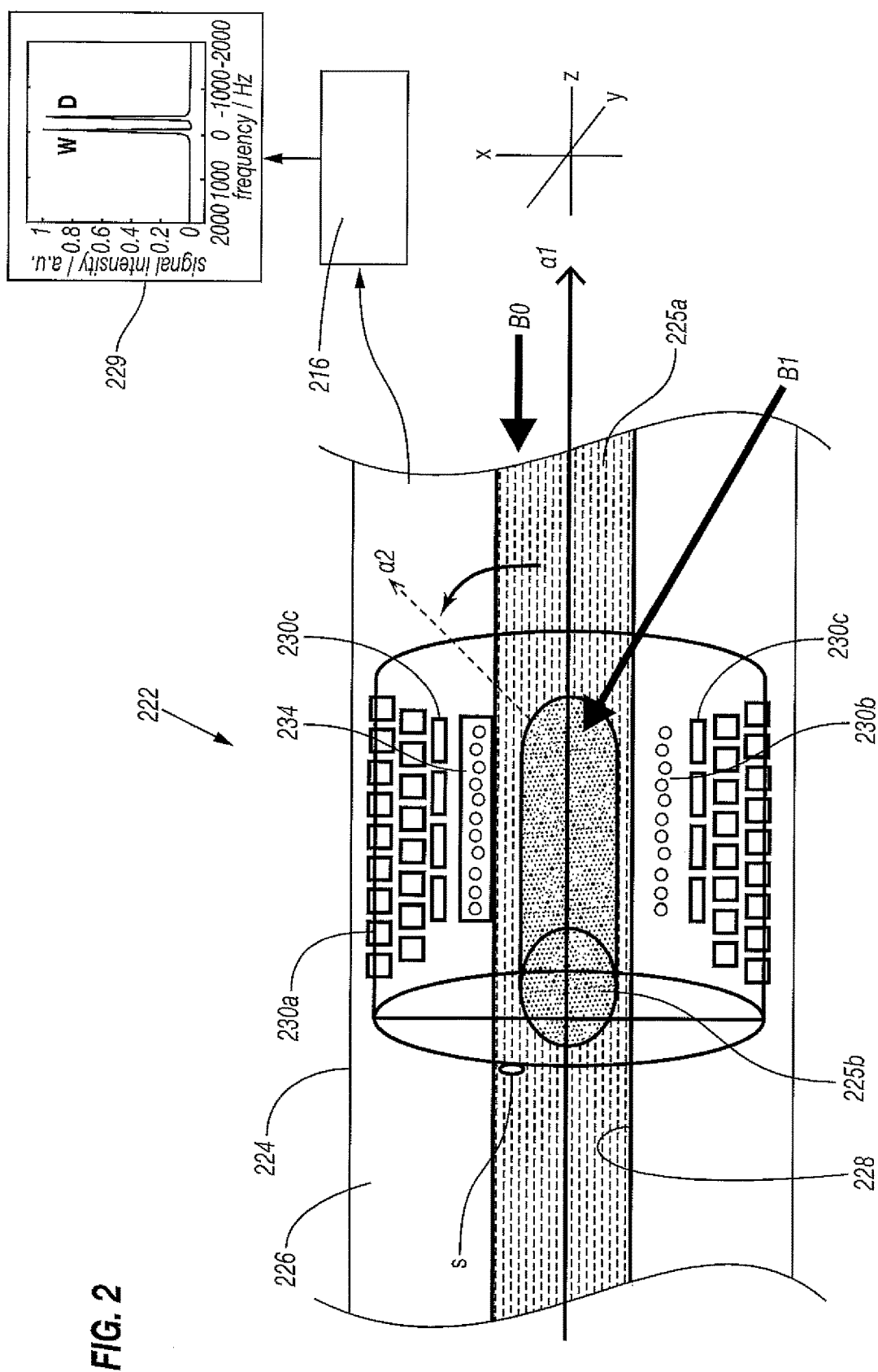
FIG. 2 is a schematic diagram depicting an imager for imaging core samples taken from the subsurface formation.

FIG. 2 is a cross-sectional view of a contrast imager 222 which may be positioned downhole (see, e.g., the imager 122d of FIG. 1A) or at a surface location (e.g., stand alone, lab facility, etc.). As shown in this view, the contrast imager 222 includes a housing 224 with a sidewall 226 defining a passage 228 which may be similar to the imager 122d of FIG. 1A. The imager may be oriented in any direction to facilitate operation.

The passage 228 is shaped to receive a core sample 225b (e.g., core sample 125b of FIG. 1A) and fluid 225a (e.g., the fluid sample 125a of FIG. 1A). The core sample 225b may be a cylindrically shaped sample that may be disposed into the linear passage 228 of the housing 224 as shown, or of other shapes and/or dimensions. Devices may be provided to automatically insert and/or remove one or more samples into/out of the passage 228.

The fluid 225a may be passed through the passage 228 during testing as indicated by the axial arrow. A flowline and/or other flow control devices may optionally be provided to selectively pass the fluid 225a into the passage 228 to provide the desired core flooding. The fluid 225a may flow through the passage 228 at a desired flow rate, or be enclosed therein to remain stationary during testing. The fluid 225a may be dumped from the passage 228 as desired. The fluid 225a may be any fluid passed through the core sample 225b during testing. In an example, the fluid 225a is in situ fluid from the formation used to replicate subsurface conditions.

As indicated by the curved arrow, the imager and/or the core sample 225b may optionally be rotated (e.g., by a rotating shaft driven by a motor) to change the orientation of the core sample 225b from an angle α1 to α2 during imaging. The rotation of the core sample 225b relative to the housing 224 allows for signal selection along the coordinates based on the orientation of the direction of the fields B0 and B1 to the orientation of the core sample 225b as it rotates.

The housing 224 has a sensor array including a permanent magnet 230a, a radio frequency coil 230b, and an applied magnetic field gradient(s) 230c. The permanent magnet 230a is positioned in the sidewall 226 and is radially disposed about the passage 228 to encircle the core sample 225b therein. The permanent magnet 230a may be any permanent magnet, such as a Halbach magnet, arranged to generate a magnetic field (B0) oriented to the z-axis of the passage 228.

The radio frequency coil 230b is positioned in the sidewall 226 and is radially disposed about the passage 228 to encircle the core sample 225b therein. The radio frequency coil 230b is positioned between the passage 228 and the permanent magnet 230a. The radio frequency coil 230b may be a coil arranged to generate a magnetic field B1 oscillating at a radio frequency along the x or y-axis of the passage 228. The magnetic field gradients 230c are positioned between the permanent magnet 230a and the radio frequency coil 230b.

The housing 224 may be provided with or coupled to an imaging unit 216 (e.g., surface unit 116 of FIG. 1A) for providing power, collecting data, and/or sending commands to the imager 222. The magnetic coil 230a, the radio frequency coil 230b, and the magnetic field gradients 230c may be coupled to the imaging unit 216 to provide measurements thereto. The imager 222 and/or the imaging unit 216 may be provided with communication means, such as a wired and/or wireless coupling to define a communication link therebetween.

The imaging unit 216 may have a conventional display capable of transforming the measurements into images for display. The imaging unit 216 may include, for example, a processor, a database, a telemetry unit, a power unit, and/or other electronics for operation with the imager 222. The imaging unit 216 may be incorporated into the electronics of the downhole tool (e.g., 122a of FIG. 1A) and/or the surface unit 116 (FIG. 1A). The collected measurements may be used to generate outputs, such as a plot 229. Optionally, one or more probes 234 and/or the sensors S may be provided to collect measurements. For example, the probe(s) 234 of the radio frequency coil 230b may be selectively provided with single and/or multiple resonant frequencies, for example to allow for detection of multiple nuclei.

The imaging unit 216 may be used to collect image parameters (e.g., distribution of fluids, residual oil saturation, etc.) from the imager 222 and subsurface parameters (e.g., composition, temperature, pressure, etc.) from the sensors (S). The imaging and/or collected measurements may be used to perform various formation evaluations, such as imaging, fluid analysis, effluent analysis, compressed sensing, etc. For example, the collected data may be used to derive subsurface parameters, such as resistivity and permeability.

Contrast Imaging

Evaluations may be performed using various contrast imaging techniques, such as relaxation and diffusion imaging. Such techniques may involve, for example, analysis of relaxation times $T_1$ and $T_2$ for the generated images. Imaging parameters may be generated using, for example, techniques that rely on differences in NMR measureable quantities, such as relaxation times and diffusion coefficients (D) to provide contrast between hydrocarbons and aqueous fluid. The NMR measurement may include a baseline measurement used in petrophysical work, such as the relaxation time $T_2$. $T_2$ may be a measure of the decay of bulk magnetization created in the system through the application of radio frequency excitations. The decay in magnetic coherence may be caused by interactions of the nuclear spins with varying magnetic fields produced by static field inhomogeneities as well as inter- and intra-molecular motions.

In a porous rock environment, hydrocarbons and aqueous fluid may have similar $T_2$'s. Techniques used to provide contrast between fluid phases may, therefore, probe secondary fluid properties, such as the relaxation time $T_1$ and the diffusion coefficients of the respective fluids. $T_1$ may be a measure of how well the molecules of a fluid exchange energy with the environment. A long $T_1$ may indicate a weak coupling, while a short $T_1$ may indicate a strong coupling. As such, $T_1$ relaxation times may be dependent on molecular properties, such as size, and the larger hydrocarbon molecules may exhibit longer $T_1$'s. The self-diffusion coefficients of fluids, such as aqueous fluid, liquid hydrocarbons, and gaseous hydrocarbons, may be quite different and may be used to differentiate between fluid phases present in a rock sample. In these cases, multi-dimensional relaxation measurements plotting $T_1$ vs $T_2$ or D vs $T_2$ may be used provide the desired contrast Evaluations of the images may be performed using NMR core analysis and/or spectroscopic methods. Such evaluations may be used to provide a desired fluid phase differentiation on bulk samples. These evaluations may be done, for example, for standard spin echo imaging sequences, such as spin-warp. Examples of spin-warp are described in Edelstein, W. A., Hutchison, J. M. S., Johnson, G. & Redpath, T., Spin warp NMR imaging and applications to human whole-body imaging, *Physics in Medicine and Biology* 25, 751 (1980)].

In order to provide information on the spatial distribution of these fluids, one-dimensional spatially resolved $T_2$ distributions can be used to provide fluid discrimination during core floods. To provide desired separation when $T_2$ contrast between the fluids is low, multi-dimensional relaxation measurements, such as $D$-$T_2$ and $T_1$-$T_2$, may be performed. These may provide bulk measurements. Further information on distributions of hydrocarbons and aqueous fluid beyond the relative volumes may be performed as is described further herein.

Spatial distribution of phases in a single core plug may be determined by using chemical dopants in injected aqueous fluid to provide relaxation contrast. In an example, chemical dopants containing species, such as $Cu^{2+}$, $Mn^{2+}$, or $Gd^{3+}$, may be used. These substances may be used to reduce the relaxation time of aqueous fluid, and to provide a differentiation between various fluids, such as aqueous fluid and hydrocarbons.

In another example, in systems that exhibit different $T_1$ values, $T_1$ nulling may be used to suppress the signal from one of $T_1$ environments present in the sample. The timing of the RF excitation pulses may be set such that the magnetization and resulting MRI signal from one $T_1$ environment is signal suppressed. The core sample may be saturated with multiple fluid phases with sample fluid, such as a fluid having a single, well-defined $T_1$.

In yet another example, chemical selectivity of NMR measurements may be used to differentiate the formation fluids. The NMR response of a given species depends on the gyromagnetic ratio of that spin, a quantity that is unique to each NMR-active species. In a first case, $D_2O$ may be used instead of $H_2O$ in the injected brine to remove the contribution of aqueous fluid to the image. In another case, the imaging may be done on the hydrogen (or other NMR-active nucleus, such as sodium, $^{23}Na$ or carbon $^{13}C$) present in the formation fluid.

Examples of contrast imaging are provided in Mitchell, J., Chandrasekera, T. C., Holland, D. J., Gladden, L. F. and Fordham, E. J., Magnetic resonance imaging in petrophysical core analysis, *Physics Reports,* 526, pp. 165-225 (2013). Other existing techniques may be used for evaluation, such as those described in U.S. Pat. Nos. 9,133,709, 8,499,856, 6,220,371 and 4,769,602.

Chemically-Selective Imaging

Evaluations may also be performed using chemically-selective imaging techniques to generate independent images of fluids, such as hydrocarbon and aqueous (brine), within a formation using an imager (e.g., imagers 122d, and 222 of FIGS. 1A and 2, respectively). The chemically-selective imaging technique exploits the difference in the chemical shift in the NMR spectrum to differentiate between fluids in the core sample.

The chemically-selective imaging involves: 1) contrasting hydrocarbon images and aqueous (brine) images based upon differences in chemical shift in the nuclear magnetic resonance (NMR) spectrum, and 2) acquiring 1, 2 or 3D images on a timescale that reduces pixel blurring between successive oil-water images during drainage and imbibition experiments at representative reservoir flow rates (e.g., at $v_i$, =1 ft day$^{-1}$ (0.304 m day$^{-1}$)). To achieve this, MRI pulse sequences (e.g., rapid acquisition with relaxation enhancement (RARE)) may be used in combination with compressed sensing (CS).

Figure 3A:
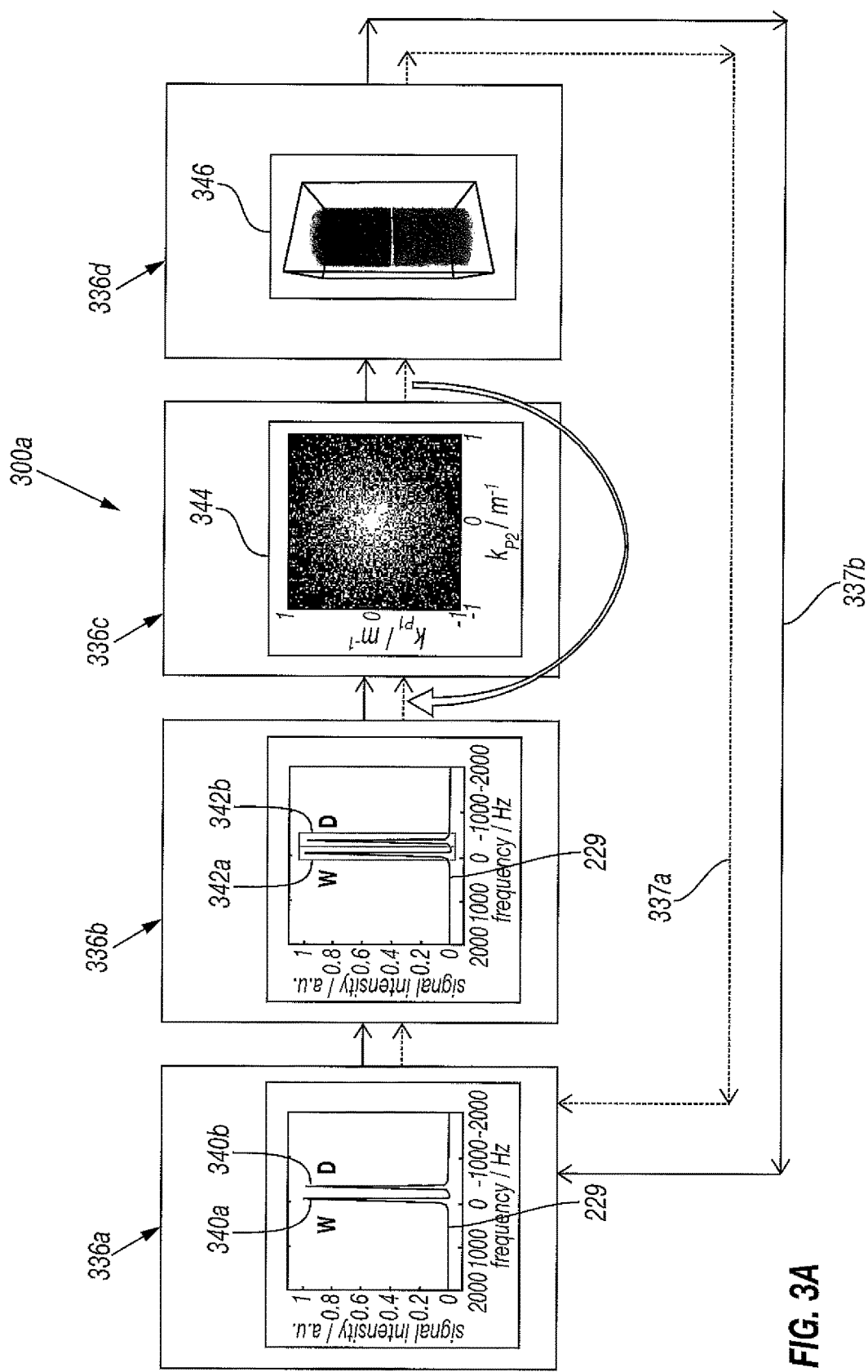
FIGS. 3A and 3B are schematic diagrams depicting imaging processes for imaging fluid in the core sample.
Figure 3B:
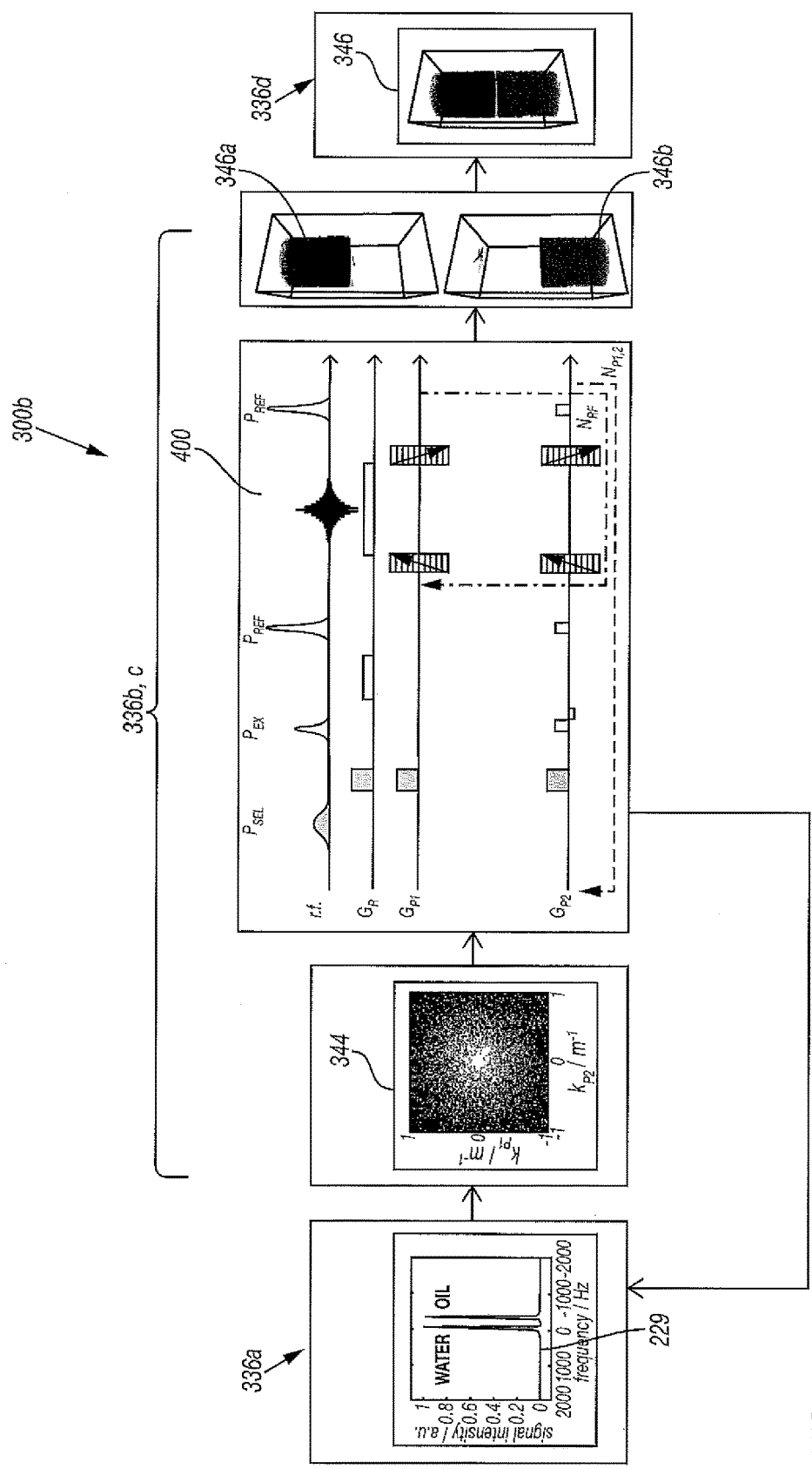

FIGS. 3A and 3B are flow charts depicting chemically-selective imaging processes 300a,b which may be performed using the imagers 122d, and 222, respectively, of FIGS. 1A and/or 2 to image fluids in the core sample. The process 300a of FIG. 3A includes a measurement phase 336a, a signal selection phase 336b, an image acquisition phase 336c, and an image display phase 336d. The process 300a may be performed for one or more fluids in the core sample. As indicated by the dotted and smooth arrows 337a,b, part or all of the process 300a may be selectively repeated for one or more fluid (e.g., 337a—aqueous fluid, 337b hydrocarbon) in the core sample.

The measurement phase 336a involves collecting measurements, such as the plot 229 of FIG. 2 generated by the imaging unit 216. The graph 229 as shown plots signal intensity (a.u.) (y-axis) versus frequency (Hz) (x-axis) generated by the imager 222. The resulting line shows peaks 340a,b that correspond to a composition of the fluid. In the example shown, the peaks 340a,b corresponding to aqueous fluid (W) and hydrocarbon (D-dodecane) with peaks at 0 Hz at 300 Hz, respectively.

The signal selection phase 336b involves selective excitation of the magnetization from either the aqueous or hydrocarbon phase. The selection may be made to indicate which fluid is to be imaged. For example, when performing the process 300a for aqueous fluid according to line 337a, the water peak 340a may be selected using box 342a. In another example, when performing the process 300a for hydrocarbon according to line 337b, the hydrocarbon peak 340b may be selected using box 342b.

The image acquisition phase 336c involves acquiring the raw k-space data 344 corresponding to the fluid distribution through the core sample using MRI pulse sequences. The sample pattern 344 is a plot of $k_{p1}$ m$^{-1}$ (y-axis) versus $k_{p2}$ m$^{-1}$ (x-axis) which indicates the data points that must be measured during the image acquisition. The data points on plot 344 indicate the locations of points to be acquired. The intensity of the light regions indicate where data is sampled; whereas, the dark regions indicate not sampled. This data may be captured using fast data acquisition and reconstructed using compressed sensing to generate images as described further herein.

The image display phase 336d involves generating an image 346 of the formation fluid within the core sample. Depending on the time available, the image 346 may be acquired using a standard imaging technique, or an image generated by fast acquisition with compressed sensing reconstruction of the acquired data. While a 3D image 346 is shown, the image may be a 1D or 2D image. One or more images of one or more fluids may be displayed as is described further herein. When generating the images, the image acquisition phase 336c may optionally be performed at various angles.

As shown in FIG. 3B, the process 300b may involve pulse sequencing 400. The process 300b involves the same measurements phase 336a, a combined signal selection and image acquisition phase 336b,c, and the image display phase 336d. A portion of the process 300b is repeated as indicated by the arrows 337a,b for various fluids.

Because the pulse sequence 400 may selectively capture data for certain fluids, the pulse sequence 400 may be used to determine which fluids are being imaged. The process 300b may be repeated at different pulse frequencies to excite the selected fluid, such as water 346a and hydrocarbon 346b as shown.

Figure 4A:
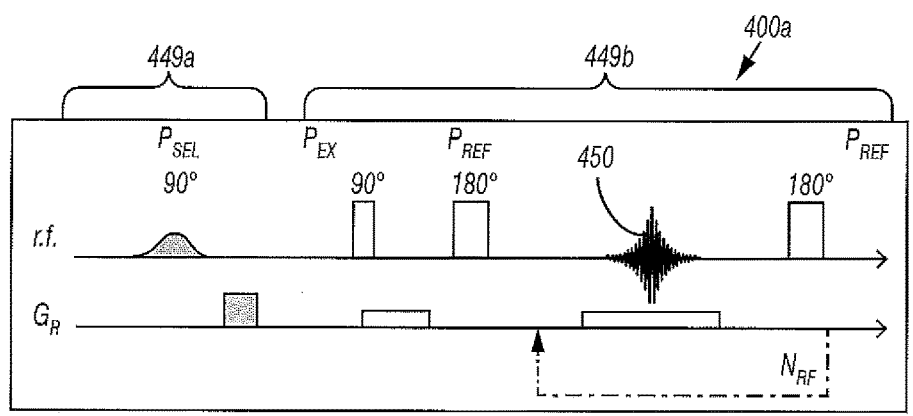
FIGS. 4A-4C are schematic diagrams depicting 1D, 2D, and 3D pulse sequences, respectively, generated during the imaging.
Figure 4B:
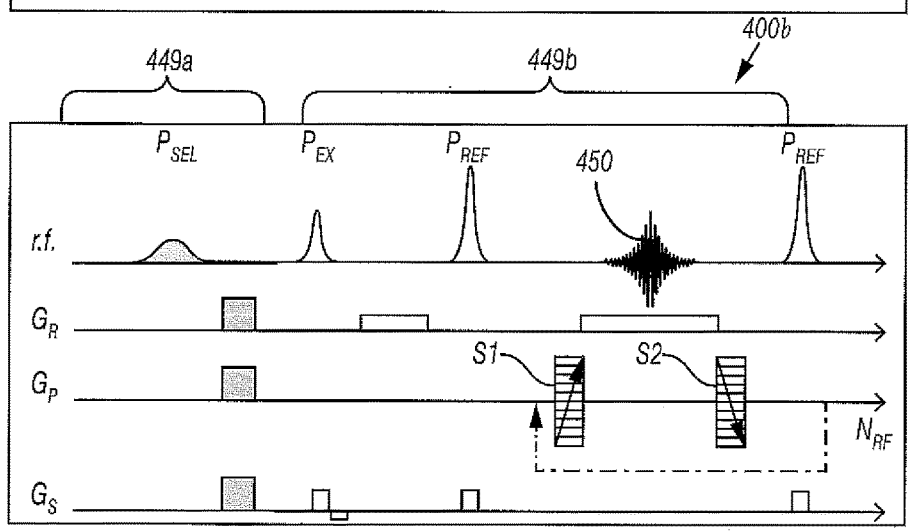
Figure 4C:
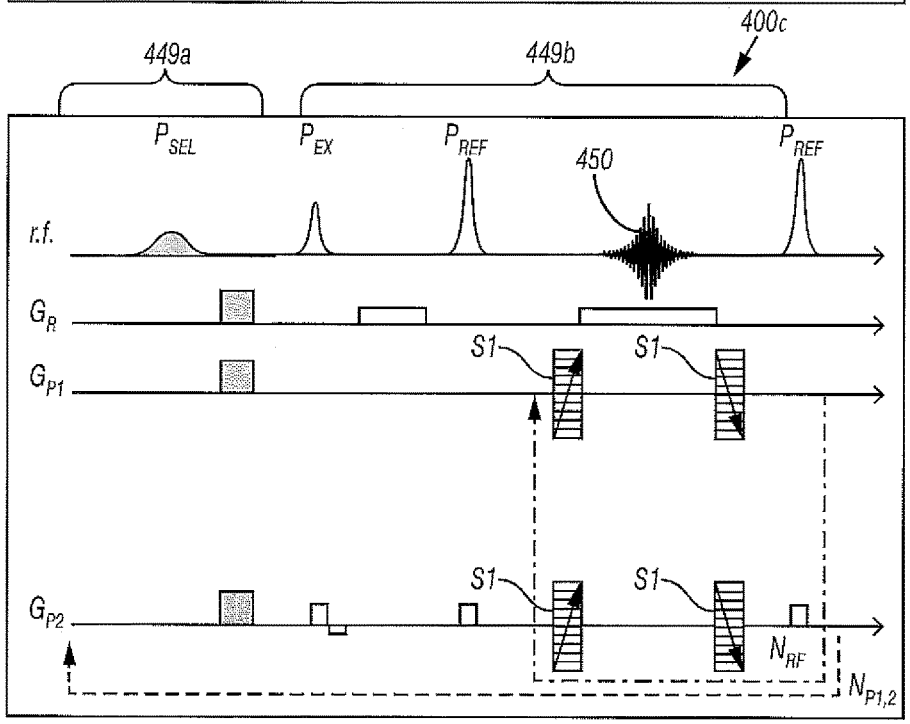

FIGS. 4A-4C are graphs depicting various pulse sequences 400a,b,c that may be used during the image acquisition phase 336c to acquire the raw data of the hydrocarbon and aqueous phase distribution of FIG. 3. FIG. 4A shows a 1D sequence. FIG. 4B shows a 2D sequence. FIG. 4C shows a 3D sequence.

Each of the pulse sequences 400a-c includes radio frequency pulses (rf) from the RF coils and one or more of the applied magnetic field gradients ($G_R$, $G_P/G_{P1}$, $G_S/G_{P2}$) (e.g., 230b,c of FIG. 2). The pulse sequences may be applied to selectively excite a certain chemical species (e.g. oil or brine) present in the sample. The magnetic fields include a read gradient ($G_R$) and phase gradients ($G_P/G_{P1}$, $G_S/G_{P2}$) which are applied for a period of time to enable spatial-encoding of the nuclear spins.

Each of the pulse sequences also include a portion 449a which represents the chemically-selective preconditioning and portions 449b representing the excitation portion of the pulses. The pulses sequences 400a-c are performed in various shapes and at various degrees to generate different perspectives of the sample being imaged. Each of the pulse sequences includes: $P_{SEL}$—a selective excitation pulse, $P_{EX}$—a non-selective excitation pulse, $P_{REF}$—a refocusing pulse. For example, for pulse sequence used in fast acquisition, the 180° refocusing RF pulses may be repeated $N_{RF}$ times to sample multiple line of k-space from a single excitation of the system.

As shown in FIGS. 4A-4C, each pulse sequence has different shapes. Radio frequency (re pulses create spin echoes 450 which are induced by polarized H atoms. Different phase gradients ($G_P/G_{P1}$, $G_S/G_{P2}$) may be used to enable spatial encoding of the spins.

As shown in the 1D version of FIG. 4A, the pulse sequence 400a includes an rf pulse for excitation and a read gradient ($G_R$) to enable spatial resolved information in the direction of the read gradient only. The rf field may be added to the magnetic field in pulses shot in microseconds. The shape of the pulses on radio frequency line r.f. include square pulses with broadband that affect the entire pulses. The read gradient $G_R$ is repeated only once for generating a 1D image.

FIG. 4B shows a 2D version of a pulse sequence 400b including the rf pulse and the $G_R$ pulse, with additional $G_P$ and $G_S$ pulses. The shape of the pulses on radio frequency line r.f. are Gaussian to affect only specific regions of the sample. This version also depicts gradient iterations S1, S2 along gradient line G.

These gradient iterations indicate that the $G_P$ is repeated in order to generate the 2D image. The phase gradient ($G_P$) are iterated $N_{RE}$ times for the iterations S1, S2. The 180° refocusing pulse may be repeated $N_{RE}$ times. Information may be acquired as needed by changing the strength of the various gradients. Each time the read gradient ($G_R$) and the slice gradient ($G_S$) are the same, the amplitude of the phase gradient ($G_P$) may be changed and then iterated through the various gradients values (S1 and S2) to generate a 2D image.

FIG. 4C shows a 3D version of the pulse sequence 400c including the rf pulses and the read gradient $G_R$, with additional first and second phase-encoding gradients, $G_{P1}$ and $G_{P2}$. In this version, the $G_{P1}$ and $G_{P2}$ pulses each include gradient iterations S1, S2 indicating that these pulses are repeated $N_{RF}$ times in order to generate the desired 3D image. For 3D images, all combinations of $G_{P1}$ and $G_{P2}$ may be iterated with the same read gradient.

The pulse sequences 400a,b,c depict example chemically-selective RARE pulse sequences. The pulse sequences 400a-c have k-space frequencies encoded in the read direction ($k_R$) and phase encoded in $k_{P1}$ and $k_{P2}$ as depicted in the image 344 of FIG. 3A. Upon the application of the read gradient ($G_R$) and phase gradients ($G_P/G_{P1}$, $G_S/G_{P2}$) points of the plot 344 are generated. For the 3D pulse sequence (FIG. 4C), the amplitude of the phase encoding gradients, $G_{P1}$ and $G_{P2}$ determine which data points on the plot 344 are sampled. The image display phase 336d uses compressed-sensing to reconstruct a fluid image from the core image. The duration and amplitude of the gradients may be varied to control the spatially resolved information that is acquired. By changing these, the field of view and area imaged and resolution may be adjusted to provide a desired focus level about the sample.

MRI acquisition techniques may be used to under sample data to reduce data collection time and compressed sensing can be used to reconstruct a full image from under sampled data. Image acquisition techniques may include, for example, Rapid Acquisition with Relaxation Enhancement (RARE), Echo Planar Imaging (EPI), spin warp, and/or other acquisition techniques) and the temporal resolution can be enhanced further by employing under-sampling and compressed sensing reconstructions. Examples of RARE are described in Hennig, J., Nauerth, A. & Friedburg, H, RARE imaging: a fast imaging method for clinical MR. *Magnetic resonance in medicine: official journal of the Society of Magnetic Resonance in Medicine/Society of Magnetic Resonance in Medicine* 3, 823-833 (1986); examples of EPI are described in Mansfield, P. Multi-planar image formation using NMR spin echoes, *Journal of Physics C: Solid State Physics* 10, L55-L58 (1977); and examples of spin warp are described in Edelstein, W. A., Hutchison, J. M. S., Johnson, G. & Redpath, T., Spin warp NMR imaging and applications to human whole-body imaging, *Physics in Medicine and Biology* 25, 751 (1980).

Compressed sensing in MRI is based on the following requirements, for example, (1) aliasing artifacts (e.g., the sample data) in the linear reconstruction must be incoherent and noise-like; (2) the desired image exhibits transform sparsity; and (3) the image is reconstructed using a non-linear algorithm that enforces sparsity and consistency with the acquired k-space data.

Assuming the image reconstructed is given by x which is related to the acquired k-space measurements via the following Equation (1):

$$SFx+v=y, \quad (1)$$

where S is the sub-sampling pattern, F is the Fourier transform that maps the image into k-space, v is the normally-distributed noise (standard deviation a and zero mean) and y is the vector that contains the acquired k-space measurements.

Due to under-sampling and the presence of noise, Equation 1 may be an ill-posed problem and, therefore, linear image reconstruction methods, such as the inverse Fourier transform, which may be employed for the image reconstruction of a fully-sampled k-space data set, may result in an image containing aliasing artefacts due to violation of Nyquist criterion. Therefore, an approximate solution to x may be sought by using a variational regularization approach balancing the model (Equation 1) and prior assumptions of x in terms of a regularization functional J given by:

$$x_\sigma \in \underset{\sigma}{\mathrm{argmin}} J(x), \quad (2)$$

subject to $\|SFx - y\|_2 \le \sigma$.

The role of the inequality constraint enforces consistency with the acquired k-space data and the regularization term J incorporates prior information on the reconstruction of $x_o$, which may be needed to counteract any ill-posedness of the problem.

In the case of the CS reconstruction, the prior information is that the image can be sparsely represented either implicitly or in an appropriate transform domain. The choice of the regularization functional (J) that is used to map the image into the transform domain may depends on the nature of image to be reconstructed. For instance, a non-smooth regularizer, such as Total Variation (TV), may be more suited to an image with sharp-edges whereas a smooth regularizer, such as the Daubechies wavelet transform, lends itself well to images in which the pixel intensities change more gently. In the present study, TV has been used as the regularization functionals, J(x), as will now be discussed.

Total Variation penalizes the 1-norm of the 2-norm of the finite different approximation of the gradient ($\nabla x$) of the image as given by:

$$J(x) = TVx = \|\nabla x\|_{2,1}. \qquad (3)$$

Herein, Neumann boundary conditions were set for the CS reconstructions. Other regularization functions, such as wavelet transforms, can be used.

Generally, the Tikhonov-Regularization scheme for the approximation of x is written as shown below:

$$x_\alpha \in \operatorname{argmin}\left\{\frac{1}{2}\|y - SFx\|_2^2 + \alpha J(x)\right\} \qquad (4)$$

and the regularization parameter α (always positive) weights the influence of the fidelity and regularization terms in Equation 4. In the present study, a modification of Equation 5 to include Bregman iterations has been implemented as described by Equations (5a),(5b):

$$x_\alpha^k \in \operatorname{argmin}\left\{\frac{1}{2}\|y^k - SFx\|_2^2 + \alpha J(x)\right\}, \qquad (5a)$$

$$y^k = y^{k-1} + y - SFx_\alpha^k. \qquad (5b)$$

Using the Bregman approach, a series of k problems (Equation 5a) are solved with the residual added to the k-space data, y, after each iteration (Equation 5b). See, e.g., M. Benning, L. F. Gladden, D. J. Holland, C.-B. Schonlieb, T. Valkonen, Phase reconstruction from velocity-encoded MRI measurements—a survey of sparsity-promoting variational approaches, Journal of Magnetic Resonance. 238 (2014) 26-43.

Compressed sensing may be used in combination with MRI pulse sequences for example CS-RARE, in which k-space is under sampled. Examples of Compressed Sensing (CS) are described in Lustig, M., Donoho, D. L., Santos, J. M. & Pauly, J. M, Compressed Sensing MRI. *IEEE Signal Processing Magazine* 25, 72-82 (2008); and Lustig, M., Donoho, D. & Pauly, J. M., Sparse MRI: The application of compressed sensing for rapid MR imaging. *Magnetic resonance in medicine: official journal of the Society of Magnetic Resonance in Medicine/Society of Magnetic Resonance in Medicine* 58, 1182-95 (2007).

The image acquisition and compressed sensing techniques may be used in combination with imaging of subsurface materials. Examples of imaging of subsurface materials include Chang, C. T., Edwards, C. M., 1993, Proton MR Two-Component Chemical Shift Imaging of Fluids in Porous Media, *The Log Analyst*, 34, pp. 20-28; Dereppe, J. M., Moreaux, C., Chemical Shift Imaging of Fluid Filled Porous Rocks, *Magnetic Resonance Imaging*, 9, pp. 809-813 (1991); Dereppe, J. M., Moreaux, C., 2D Spin-Echo and 3D Chemical-Shift-Imaging Techniques for Analysis of Oil-Water Replacement in Limestone. *Journal of Magnetic Resonance*, 91, pp. 596-603 (1991); Maudsley, A. A., Hila,l, S. K., Perman, W. H., Simon, H. E., Spatially Resolved High Resolution Spectroscopy by "Four-Dimensional" NMR. *Journal of Magnetic Resonance*, 51, pp. 147-152 (1983); and Dechter, James J., Komoroski, Richard A., Ramaprasad, S., Use of Presaturation for Chemical-Shift Selective Imaging of Individual Fluids in Sandstone and Carbonate Cores, *Journal of Magnetic Resonance*, 93, pp. 142-150 (1991).

The chemically-selective preconditioning section 449a and a RARE imaging pulse sequence section 449b may be used to facilitate the acquisition. Through the use of chemically-selective radio frequency (r.f.) pulses and homospoil gradients, the signal from either various fluids (e.g., hydrocarbon and aqueous fluid) can be effectively suppressed prior to the imaging section of the pulse sequence.

FIGS. 4B and 4C show the RARE pulse sequences for 2D and 3D acquisitions, respectively. For 2D applications, under-sampling of k-space in the phase encoding direction (P1) can be performed whereas for the latter, under-sampling of k-space can be performed in both phase encoding directions (P1 and P2). In both cases, k-space is fully sampled in the read direction (R). The under-sampled k-space data is reconstructed using compressed sensing.

In a 2D pulse sequencing example, the chemically-selective section 449b of FIG. 4B includes a Gaussian shaped rf pulse (r.f.) used to selectively excite one of the phases, followed by homospoil gradients ($G_R$, $G_P$, $G_S$) to destroy the magnetization. To demonstrate the chemically-selective imaging two-dimensional (2D) slice images have been acquired. A first image may include a reference image of aqueous fluid and hydrocarbon with no chemically-selective preconditioning. A second image may include aqueous fluid and hydrocarbon independently. Table 1 depicts the experimental parameters used to generate 2D images:

TABLE 1

| | 2D | | |
|---|---|---|---|
| | Reference image | Chemically-selective images | |
| | Aqueous fluid and dodecane | Aqueous fluid | Dodecane |
| Field of view (y)/mm | 80 | 80 | 80 |
| Field of view (x)/mm | 50 | 50 | 50 |
| Slice thickness (z)/mm | 2 | 2 | 2 |
| In-plane resolution (y)/mm pixel$^{-1}$ | 0.39 | 0.39 | 0.39 |
| In-plane resolution (x)/mm pixel$^{-1}$ | 0.31 | 0.31 | 0.31 |
| Excitation pulse duration, $P_{EX}$/μs | 512 | 512 | 512 |
| Refocusing pulse duration, $P_{REF}$/μs | 512 | 512 | 512 |
| Excitation pulse power, $PL_{EX}$/dB | 27 | 27 | 27 |
| Refocusing pulse power, $PL_{REF}$/dB | 21 | 21 | 21 |
| Selective excitation pulse duration, $P_{SEL}$/μs | — | 8192 | 8192 |
| Selective excitation bandwidth, $BW_{SEL}$/Hz | — | 530 | 530 |
| Selective excitation pulse power, $PL_{SEL}$/dB | — | 44 | 44 |
| Selective excitation pulse offset, $O_{SEL}$/Hz | — | −350 | 0 |

Table 1 indicates that, by suppressing the signal from the hydrocarbon only aqueous fluid is detected. Conversely, by suppressing the signal from the aqueous fluid, only hydrocarbon is detected.

The number of 180° degree refocusing pulses applied for each acquisition may be determined by the RARE factor ($N_{RF}$) and the total number of r.f. excitations ($N_{EX}$) required to sample k-space is given by the total number of points in the two phase encoding directions, $N_{P1,2}$ divided by $N_{RF}$. The images may be generated using a rapid sequencing by using fast imaging sequences, such as RARE, EPI, etc., and the temporal resolution can be enhanced further by employing under-sampling and subsequently using compressed sensing for image reconstructions. The temporal resolution of standard imaging sequences may also be enhanced by using compressed sensing, such as CS-RARE. Both RARE and EPI may use multiple lines of k-space acquired from an individual excitation. The practical limit on the number of lines of data that can be acquired from each excitation, and correspondingly the acquisition time acceleration, may be determined by the relaxation times of the sample under investigation. The transverse relaxation times for the fluid-saturated rock core samples, which are the subject of the present invention, are expected to be in the range of tens to hundreds of milliseconds. Considering a RARE acquisition of a water-saturated rock core with a $T_2=150$ ms, with an echo time $T_E=4$ ms, it may be reasonable to suggest that 64 lines of k-space can be acquired from each excitation.

By using compressed sensing (CS), a signal with a sparse representation, such as an image, can be recovered from a number of measurements sampled below the Nyquist rate. Therefore, applying CS to ultra-fast MRI acquisitions, under sampling k-space may lead to further reductions in acquisition image times, thus enabling dynamic processes, such as the laboratory core flood, to be studied where the temporal resolution is greater still.

In a 3D example as shown by FIG. 4C, various pulsing configurations may be provided, for example, when it is desirable to obtain information on the fluid distribution within the rock core. A comparison of Spin-warp, RARE, and CS-RARE techniques applied to an MRI protocol to monitor the fluid distribution in a laboratory core flood experiment is shown below:

TABLE 2

| 3D | | | |
|---|---|---|---|
| | (1) Spin-Warp | (2) RARE | (3) CS-RARE |
| Pixels in read direction, $N_R$/— | 256 | 256 | 256 |
| Pixels in first phase encoding direction, $N_{P1}$/— | 128 | 128 | 128 |
| Pixels in first phase encoding direction, $N_{P2}$/— | 128 | 128 | 128 |
| Number of lines of k-space sampled per excitation, $N_{EX}$/— | 1 | 64 | 64 |
| Recycle delay, TR/s | 1.6 | 1.6 | 1.6 |
| Number of scans, NS/— | 8 | 8 | 8 |
| k-space sampling fraction, SF/% | 100 | 100 | 25 |

The total image acquisition time ($T_{ACQ}$) can be calculated using Equation 6:

$$T_{ACQ} = NS \times TR \times \left[\frac{SF \times (N_{P1} \times N_{P2})}{N_{EX}}\right] \quad (6)$$

Using equation 6, Table 3 shows total acquisition time for each of the techniques of Table 2:

TABLE 3

| | (1) Spin-Warp | (2) RARE | (3) CS-RARE |
|---|---|---|---|
| Acquisition time, $T_{ACQ}$/min | 3495 | 55 | 14 |

The total acquisition time may be minimized using CS-RARE. To this end, the amount of fluid injected over the course of the three acquisition times may be calculated for the case of a theoretical core flood as shown by Table 3. The relevant sample properties and experimental conditions are listed in Table 4:

TABLE 4

| Plug diameter, D/mm | 38 |
|---|---|
| Plug length, L/mm | 76 |
| Plug volume, V/ml | 87 |
| Rock porosity, $\phi$/% | 23 |
| Pore volume, P.V./ml | 20 |
| Interstitial velocity, $v_i$/ft day$^{-1}$ | 1 |
| Injectant flow rate, Q/ml min$^{-1}$ | 0.06 |

The total number of pore volumes (N.P.V) of fluid injected over the course of the image acquisitions for each of the three cases considered, may be calculated using Equation 7 and is summarized in Table 5.

$$N.P.V = \frac{T_{ACQ} \times Q_I}{P.V.} \quad (7)$$

The total number of pore volumes (N.P.V) of fluid injected over the course of the image acquisitions for each of the three cases considered is calculated using Equation 8 and is summarized in Table 5:

TABLE 5

| | (1) Spin-Warp | (2) RARE | (3) CS-RARE |
|---|---|---|---|
| Number of P.V. injected, N.P.V/ml | 10.50 | 0.16 | 0.04 |

Table 5 indicates that a significant reduction in sample volume may be achieved using rapid imaging with compressed sensing, such as CS-RARE, and that such images may be more representative of the fluid saturation at specific time points in the core flood.

Figure 5C:
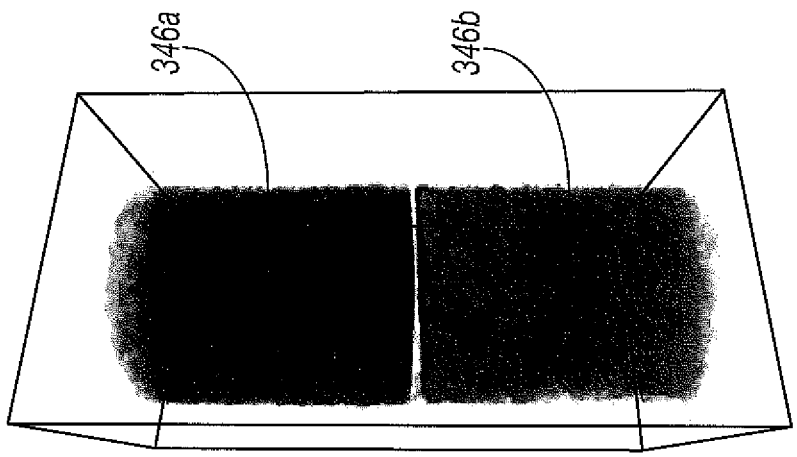
FIGS. 5A-5C are images of fluids in the core sample.
Figure 5B:
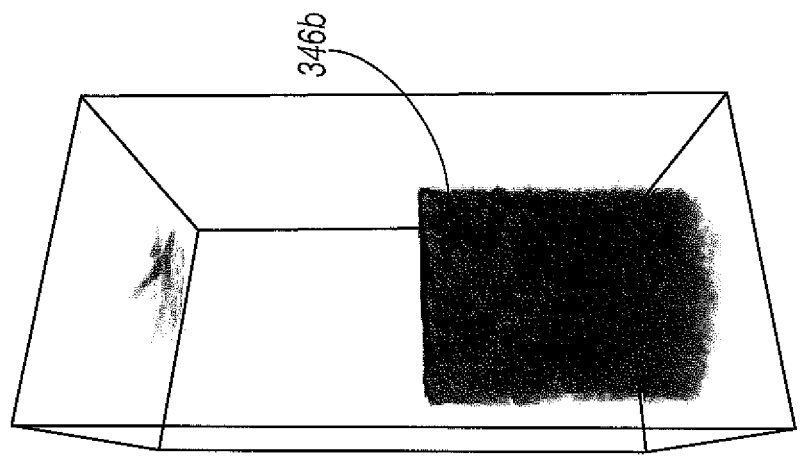
Figure 5A:
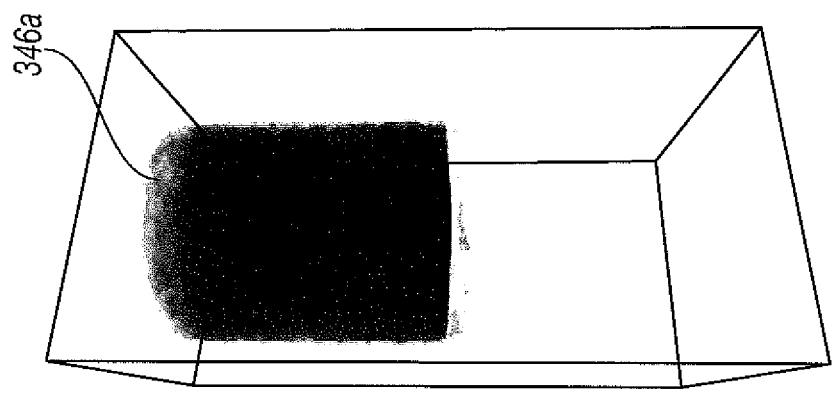

FIGS. 5A-5C show the 3D image 346 in greater detail. These images may be used to individually depict each of the fluids hosted within the pores of the formation. As shown in these figures, the chemically-selective 3D CS-RARE MRI method is implemented to independently image hydrocarbon and aqueous fluid within a core sample using imager 222 of FIG. 2 in a laboratory core-flooding experiment at representative reservoir conditions. The 3D pulse sequence of FIG. 4C is used to generate MRI measurements according to the plot 344 of FIG. 3A. The white pixels of 344 determine the values of $G_{P1}$ $G_{P2}$ which in turn determine which data points need to be acquired. The data is then processed through compressed sensing to generate images of FIGS. 5A-5C. FIG. 5C shows the combined fluid images generated by this technique.

The original rock core was cut into two pieces with one half being saturated in aqueous fluid and the other half in hydrocarbon under ambient conditions. FIG. 5A shows a 3D fluid image 346a of aqueous phase in the core sample generated during application of the process 300 repeated along line 337b for the hydrocarbon phase. FIG. 5B shows a first half of 3D fluid image 346b of the hydrocarbon phase in the core sample generated during application of the process 300a repeated along line 337b for the hydrocarbon phase. FIG. 5C show a second half of the core sample the aqueous and hydrocarbon phases 346 *a,b* on the same plot.

In the example depicted in FIGS. 5A-5C, a chemically-selective 3D CS-RARE acquisitions for the selective imaging of a) dodecane and b) aqueous fluid imbibed in a limestone core plug is performed. The acquisition time for a) and b) is 14 minutes per image. The two images have been combined to provide an overall image of the aqueous fluid and hydrocarbon.

Table 6 below shows experimental parameters of the core sample used in generating the images of FIGS. 5A-5C:

TABLE 6

|  | Chemically-selective images | |
| --- | --- | --- |
|  | Aqueous fluid (FIG. 5A) | Hydrocarbon (FIG. 5B) |
| Field of view (z)/mm | 80 | 80 |
| Field of view (x)/mm | 50 | 50 |
| Slice thickness (y)/mm | 50 | 50 |
| In-plane resolution (z)/mm pixel$^{-1}$ | 0.39 | 0.39 |
| In-plane resolution (x)/mm pixel$^{-1}$ | 0.31 | 0.31 |
| In-plane resolution (y)/mm pixel$^{-1}$ | 0.31 | 0.31 |
| Excitation pulse duration, $P_{EX}$/μs | 512 | 512 |
| Refocusing pulse duration, $P_{REF}$/μs | 512 | 512 |
| Excitation pulse power, $PL_{EX}$/dB | 27 | 27 |
| Refocusing pulse power, $PL_{REF}$/dB | 21 | 21 |
| Selective excitation pulse duration, $P_{SEL}$/μs | 4096 | 4096 |
| Selective excitation bandwidth, $BW_{SEL}$/Hz | 560 | 560 |
| Selective excitation pulse power, $PL_{SEL}$/dB | 40.6 | 40.6 |
| Selective excitation pulse offset, $O_{SEL}$/Hz | −425 | 5 |

Table 7 below shows rock properties of the core sample used in generating the images of FIGS. 5A-5C:

TABLE 7

|  | Aqueous fluid | Hydrocarbon |
| --- | --- | --- |
| Rock type | Estaillades limestone | Estaillades limestone |
| Plug diameter, D/mm | 38 | 38 |
| Plug length, L/mm | ~35 | ~35 |
| Plug volume, V/ml | 40 | 40 |
| Imbibed volume/ml | 9.7 | 10.6 |

The images generated using the chemically-selective imaging process 300*a,b* of FIGS. 3A,3B may be compared with the relaxation imaging processes for validation. One or more imaging processes may be performed. For example, the chemically-selective imaging process may be used in cases where it may be undesirable to use $D_2O$, any ionic dopant, or other fluid that could negatively impact the condition of the rock sample, in cases where low signals may be present (e.g., due to low natural abundance or low gyromagnetic ratio), in cases where certain RF probes may be preferred, to avoid long acquisition times from standard single echo spin echo imaging sequences, etc. Other variations that may affect selection of the imaging may include suppression of signal from species that exhibit different T1 values via T1 nulling and standard spin echo imaging sequences in which a single line of a 2D k-space may be acquired for each initial RF excitation.

Variations on the process 300*a,b* may be performed. For example, the process may be performed on other NMR active nuclei, such as hydrogen, sodium, etc. This may be used in place of selecting hydrocarbons or brine based on chemical shift separation. Various pulse sequences, measurements, images, and/or other data may be compared for validation of the results. For example, relaxation imaging results may be compared with chemically-selective imaging results.

Imaging may be used in combination with measurements sensed with the sensor S, such as the fluid analyzer, such that a distribution of hydrocarbon and brine pore fluids can be determined. Effluent analysis can also be performed using the measurements from the optical fluid analyzer. The formation evaluation may be used to plan oilfield operations, such as designing enhanced oil recovery (EOR) (e.g., injection) to facilitate production.

FIG. 6 is a flow chart depicting an example method 600 of performing hydrocarbon operations. The method 600 may be performed using, for example, the imager 122*d*, 222 of FIGS. 1A and/or 2. The method involves 654—positioning a core sample of the formation in an imager (see, e.g., FIGS. 1A and 2). The method also involves 655—imaging the core sample by directing a magnetic field through the passage in a magnetic direction along a longitudinal axis of the passage, selectively directing a gradient field through the passage, directing a radio frequency field through the sample in the passage in the direction orthogonal to the longitudinal axis of the passage, and selectively pulsing frequencies of the radio frequency field (FIG. 2).

The method also involves 656 selectively acquiring nuclear magnetic resonance measurements of the fluid in the core sample by selectively pulsing frequencies of the radio frequency field to the core sample and applying the magnetic field gradient to the core sample according to a pre-determined, k-space sampling plot. The selectively acquiring may involve performing fast acquisition, such as RARE. The method may also involve 657—generating an image of formation fluid in the core sample by performing compressed sensing on the acquired nuclear magnetic resonance measurements.

The selectively acquiring 656 and/or generating 657 may be performed by obtaining a spectral image of the fluid from the imaging, selecting a phase for chemically-selective imaging, acquiring an image by selecting sample points from a plot generated from the selective pulsing, and performing a reconstruction of the formation fluid within the core sample using compressed sensing of the selected sample points. The method may also involve 658—performing chemically-selective imaging to isolate the fluids, such as hydrocarbon, from the fluid image, and 660—validating the image by generating reference images using contrast imaging and comparing the generated images with the reference images, and performing oilfield operation (e.g., EOR) based on the validated image.

The method may be performed in any order, and repeated as desired. Part or all of the method may be performed. Other optional steps may be performed, such as may also involve 656—rotating the sample and repeating the imaging at various angles (FIG. 2).

While the embodiments are described with reference to various implementations and exploitations, it will be understood that these embodiments are illustrative and that the scope of the inventive subject matter is not limited to them. Many variations, modifications, additions and improvements are possible. For example, one or more image may be performed using one or more of the techniques herein. Various combinations of the techniques provided herein may be used.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

The present disclosure may be modified and practiced in different but equivalent manners apparent to those skilled in the art having the benefit of the teachings herein. Furthermore, no limitations are intended to the details of construction or design herein shown. While systems and methods are described in terms of "comprising," "containing," or "including" various components or steps, the methods can also "consist essentially of" or "consist of" the various components and steps. Whenever a numerical range with a lower limit and an upper limit is disclosed, any number and any included range falling within the range is specifically disclosed. In particular, every range of values (of the form, "from a to b," or, equivalently, "from a-b") disclosed herein is to be understood to set forth every number and range encompassed within the broader range of values. Whenever a numerical range having a specific lower limit only, a specific upper limit only, or a specific upper limit and a specific lower limit is disclosed, the range also includes any numerical value "about" the specified lower limit and/or the specified upper limit.

What is claimed is:

1. An imager for imaging fluid of a subsurface formation, the imager comprising:
   a housing having a sidewall defining a passage to receive a core sample of the subsurface formation therethrough, the housing positioned in a downhole tool, the housing having a fluid inlet to receive fluid from the subsurface formation into the passage;
   a permanent magnet positioned in the sidewall of the housing, the permanent magnet comprising magnetic coils oriented to direct a magnetic field through the passage;
   a radio frequency coil positioned in the sidewall of the housing between the permanent magnet and the passage, the radio frequency coil oriented to direct a radio frequency field through the passage;
   a magnetic field gradient positioned in the sidewall of the housing between the permanent magnet and the radio frequency coil to selectively direct a gradient field through the passage; and
   a chemically-selective imager configured to generate images of the fluid in the core sample operatively connected to the radio frequency coil to selectively pulse frequencies according to a pulse sequence whereby images of hydrocarbons and aqueous fluids in the core sample are generated based on differences in chemical shift, wherein nuclear magnetic resonance measurement is performed using compressed sensing and rapid acquisition with relaxation enhancement (RARE).

2. The imager of claim 1, wherein the radio frequency coil is distributed radially about the passage and oriented to direct the radio frequency field in a direction orthogonal to the longitudinal axis of the passage.

3. The imager of claim 1, wherein the pulse frequencies are one of 1D, 2D and 3D pulse frequencies.

4. The imager of claim 1, wherein the passage has an outlet to pass the core sample and the formation fluid from the passage.

5. The imager of claim 1, further comprising a passage inlet located in the housing disposed to receive the core sample into the passage.

6. The imager of claim 1, further comprising an imaging unit operatively connected to the imager, the imaging unit being configured to display an image of the fluid in the core sample.

7. A method of imaging fluid positioned in a subsurface formation, the method comprising:
   positioning a core sample of the subsurface formation in a passage of an imager in a downhole tool;
   flooding the core sample by passing fluid from the formation into the passage;
   imaging the flooded core sample by:
      directing a magnetic field through the passage in a direction along the longitudinal axis of the passage;
      selectively directing a gradient field through the passage;
      selectively pulsing a radio frequency field through the passage in a direction orthogonal to the longitudinal axis of the passage; and
      generating images of the fluid in the core sample during the pulsing whereby images of hydrocarbons and aqueous fluids in the core sample are generated based on differences in chemical shift, wherein nuclear magnetic resonance measurement is performed using compressed sensing and rapid acquisition with relaxation enhancement (RARE).

8. The method of claim 7, further comprising rotating the core sample and repeating the selectively pulsing.

9. The method of claim 7, further comprising validating the generated images by generating reference images of the core sample using contrast imaging and comparing the reference images with the generated images.

10. A method of imaging fluid positioned in a subsurface formation, the method comprising:
    positioning a core sample of the subsurface formation in a fluid filled passage of an imager;
    directing a magnetic field through the passage in a direction along a longitudinal axis of the passage;
    selectively directing a gradient field through the passage;
    directing a radio frequency field through the passage in the direction orthogonal to the longitudinal axis of the passage;
    selectively acquiring nuclear magnetic resonance measurements of the fluid in the core sample by selectively pulsing frequencies of the radio frequency field to the core sample and applying the gradient field to the core sample according to a pre-determined k-space sampling plot; and
    generating images of the fluid in the core sample during the pulsing whereby images of hydrocarbons and aqueous fluids in the core sample are generated based on differences in chemical shift, wherein the selectively acquiring nuclear magnetic resonance measurement is performed using compressed sensing and rapid acquisition with relaxation enhancement (RARE).

11. The method of claim 10, wherein positioning comprises positioning the imager in a downhole tool and deploying the downhole tool in the wellbore.

12. The method of claim 11, further comprising after positioning the core sample in the passage of the imager, passing fluid from the formation into the passage to fill the passage.

* * * * *